US00PP17970P3

(12) United States Plant Patent
Meilland

(10) Patent No.: US PP17,970 P3
(45) Date of Patent: Aug. 28, 2007

(54) HYBRID TEA ROSE PLANT NAMED 'MEIGROUPY'

(50) Latin Name: *Rosa hybrida*
Varietal Denomination: Meigroupy

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 31 days.

(21) Appl. No.: 11/271,944

(22) Filed: Nov. 14, 2005

(65) Prior Publication Data

US 2006/0090228 P1 Apr. 27, 2006

(51) Int. Cl.
*A01H 5/00* (2006.01)

(52) U.S. Cl. ..... Plt./134

(58) Field of Classification Search ..... Plt./134, Plt./133, 135
See application file for complete search history.

(56) References Cited

PUBLICATIONS

Official Gazette of the Community Plant Variety Office, vol. 6, Cover Page and pp. 8, 33, and 47 (Dec. 15, 2004).

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of rose plant of the Hybrid Tea Class is provided which abundantly forms on a nearly continuous basis attractive highly fragrant blossoms that are near white suffused with orange-pink in coloration. The growth habit is vigorous and erect. Very decorative dark green and semi-glossy foliage is formed that contrasts nicely with the blossom coloration. The fragrance of the blossoms is strong. The new variety is particularly well suited for forming attractive ornamentation in the landscape.

1 Drawing Sheet

Figures 1, 2, 3, 4, 5, 6, 7, 8, 9, 10, 11, 12, 13, 14, 15:
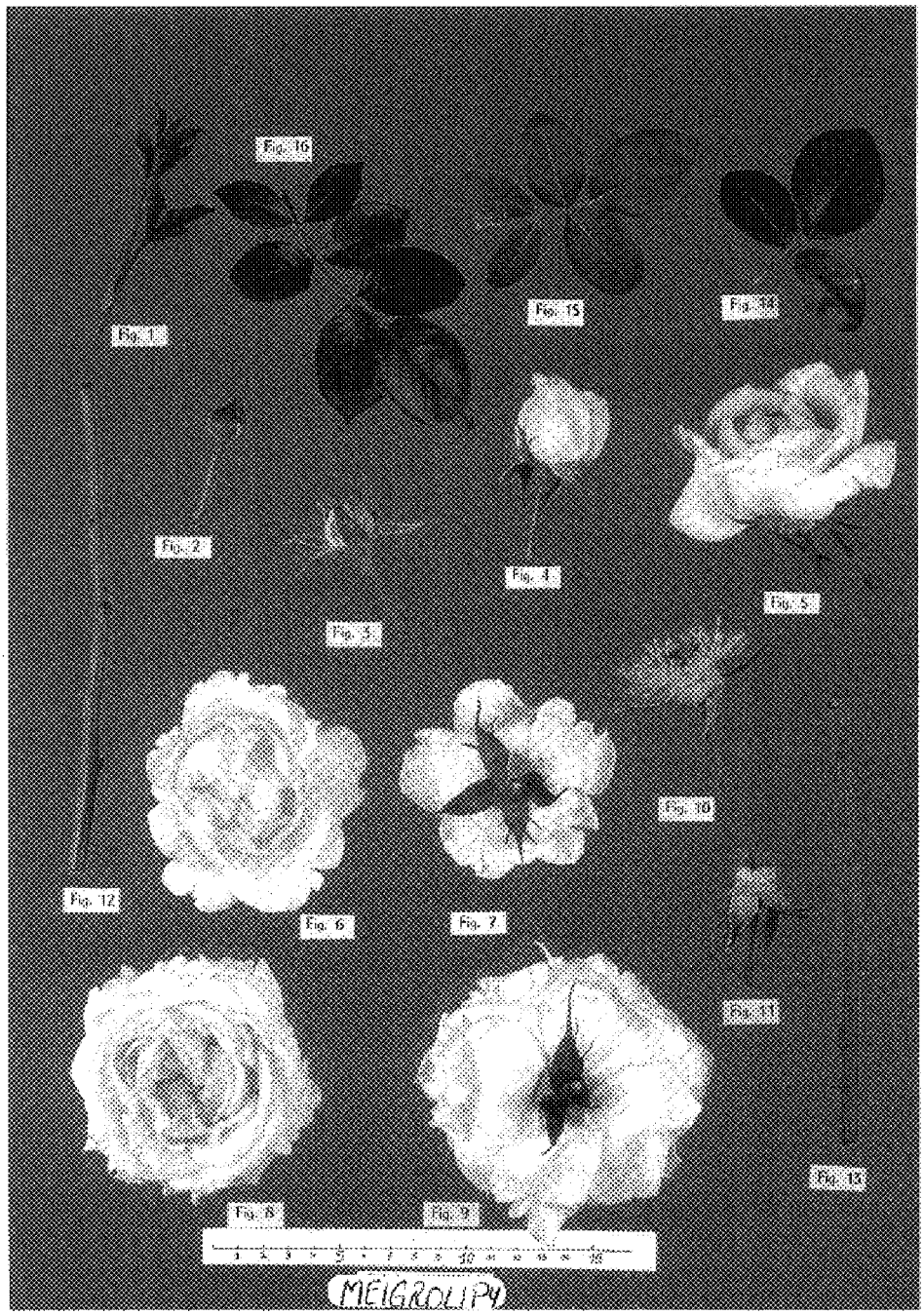

Botanical/commercial classification: *Rosa hybrida*/Hybrid Tea Rose Plant.
Varietal denomination: cv. Meigroupy.

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was product of the cross of the 'Meilivar' variety (U.S. Plant Pat. No. 7,541) and the 'Sunbelt' variety (non-patented in the United States. The male parent (i.e., the pollen parent) was the 'Meivildo' variety (U.S. Plant Pat. No. 6,895). The parentage of the new variety can be summarized as follows:

('Meilivar'×'Sunbelt')×'Meivildo'.

The seeds resulting from the above pollination were sown and small plants were obtained which were physically and biologically different from each other. Selective study resulted in the identification of a single plant of the new variety.

It was found that the Hybrid Tea rose plant of the present invention possesses the following combination of characteristics:

(a) exhibits a vigorous erect growth habit, (b) abundantly forms on a nearly continuous basis attractive highly fragrant blossoms that are near white suffused with orange-pink in coloration, (c) forms attractive dark green decorative semi-glossy foliage that contrasts well with the blossom coloration, and (d) is particularly well suited for growing as attractive ornamentation in the landscape.

The tolerance to diseases of the new variety is good.

The new variety of the present invention can be readily distinguished from its parental varieties. The 'Meilivar' variety forms blossoms that are intense yellow in coloration. The blossoms of the 'Sunbelt' variety also are yellow in coloration. The 'Meivildo' male parent forms pink blossoms having serration on the edges of the petals.

Also, the new variety can be distinguished from the 'Meidiaphaz' variety (non-patented in the United States) and the 'Meifassel' variety (U.S. Plant Pat. No. 16,951, granted Aug. 8, 2006). More specifically, the 'Meidiaphaz' variety displays dissimilar high-pointed buds, and the 'Meifassel' variety forms dissimilar high-centered blossoms.

The new variety well meets the needs of the horticultural industry and can be grown to advantage in parks and gardens.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meigroupy' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one and one-half years of age and were observed during November while budded on *Rosa froebelli* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of one and one-half year-old plants during November while budded on *Rosa froebelli* understock and growing outdoors at Le Cannet des Maures, Var, France.

Class: Hybrid Tea.

Plant:

*Height.*—Approximately 80 to 100 cm at the end of the growing season. The width is approximately 50 to 60 cm at the end of the growing season.

*Habit.*—Erect.

Branches:

*Color.*—Young stems: near Yellow-Green Group 146B. Adult wood: near Yellow-Green Group 146A.

*Texture.*—Smooth on young stems and adult stems with the adult stems commonly bearing some thorns (as described).

*Thorns.*—Configuration: upright, elongated, generally oval at the base, curved downwards on the upper surface, and concave on the under surface. Size: approximately 7 mm on average. Quantity: approximately 8 on average over an adult stem length of 17 cm. Color: near Greyed-Orange Group 165D.

Leaves:

*Size.*—A five-leaflet leaf commonly measures approximately 11.8 cm in length on average including the petiole, and approximately 10.5 cm in width on average.

*Stipules.*—Adnate, pectinate, and narrow.

*Petioles.*—Upper surface: near Yellow-Green Group 143A. Under surface: near Yellow-Green Group 143A.

*Texture.*—Slightly glandular on the under surface and without prickles on the upper surface. Length: approximately 2.4 cm on average.

*Rachis.*—Upper surface: with slight pubescence and near Yellow-Green Group 143A. Under surface: smooth and near Yellow-Green Group 143A in coloration.

*Leaflets.*—Number: 3, and most often 5 and 7. Shape: elliptic with a pointed tip and an obtuse base. Serration: single and regular (as illustrated). Texture: firm, rather thick, and semi-glossy. General appearance: dense and dark green. Size: terminal leaflets commonly measure approximately 5.5 cm in length, and approximately 3.4 cm in width. Color (young foliage): Upper surface: near Yellow-Green 146A with some reddish coloration of Greyed-Orange Group 176A. Under surface: near Yellow-Green Group 146B with some reddish coloration of Greyed-Orange Group 176A. Color (adult foliage): Upper surface: near Yellow-Green Group 147A. Under surface: near Yellow Green Group 147B.

Inflorescence:

*Number of flowers.*—Commonly one to three flowers per stem.

*Peduncle.*—Pubescent, firm and well sustains the flowers, near Yellow-Green Group 144A in coloration, approximately 2.5 to 3 cm in length on average, and approximately 0.5 cm in diameter on average.

*Sepals.*—Upper surface: smooth, and near Green Group 137A in coloration. Under surface: tomentose, and near Green Group 138B in coloration. Length: approximately 3.8 cm on average. Width: approximately 1 cm on average.

*Buds.*—Shape: generally globular. Size: large. Length: approximately 2 to 2.5 cm on average. Width: approximately 2.5 cm on average. Color upon opening: Upper surface: near Yellow Group 2D suffused with Orange Group 26C and 26D. Under surface: near Yellow Group 2D suffused with Orange Group 26C and 26D. Basal color spot: near Green-Yellow Group 1A.

*Flower.*—Shape: flat cup-shaped. Diameter: approximately 12 to 13 cm on average. Color (in the course of opening): Upper surface: near Yellow Group 4D and very slightly suffused with Orange Group 26C and 26D. Under surface: near Yellow Group 4D and very slightly suffused with Orange Group 26C and 26D. Color (basal petal spot): near Green-Yellow Group 1A on both surfaces. Color (when open): Upper surface: near Yellow Group 4D and very slightly suffused with Orange Group 26C and 26D. Under surface: near Yellow Group 4D and very slightly suffused with Orange Group 26C and 26D. Basal color spot: near Yellow Group 1A on both surfaces. Lasting quality: very long and approximately 12 to 13 days on the plant and approximately 7 to 10 days when out and placed in a vase. Petal number: commonly approximately 67 on average under normal growing conditions. Petal arrangement: imbricated. Petaloids: non observed. Petal shape: generally rounded. Petal texture: consistent. Petal drop: good, the petals commonly detach cleanly before drying. Fragrance: strong. Stamen number: approximately 136 on average. Anthers: near Orange Group 24B in coloration, approximately 0.4 cm in size, and regularly arranged around the styles. Filaments: near Yellow Group 7A in coloration, and approximately 0.8 cm in length. Pistils: approximately 130 on average. Stigmas: near Yellow-Orange Group 20A in coloration, and approximately 0.1 cm in size on average. Styles: near Yellow Group 4D in coloration, and the length is approximately 0.5 cm on average. Receptacle: near Yellow-Green Group 144A in coloration, possesses a smooth surface texture, funnel-shaped in longitudinal section, approximately 1.1 cm in length on average, and approximately 0.8 cm in width on average. Hips: formed in sparse quantity and none are available for observation.

Development:

*Vegetation.*—Strong and very vigorous.

*Blooming.*—Abundant and nearly continuous.

*Tolerance to diseases.*—Good, particularly with respect to Oidium.

*Aptitude to bear fruit.*—Slight, and no hips are available for detailed characterization.

*Hardiness.*—Grows wellin U.S.D.A. Hardiness Zone No. 6B.

I claim:

1. A new and distinct Hybrid Tea rose plant which exhibits the following combination of characteristics:

(a) a vigorous erect growth habit, (b) abundantly forms on a nearly continuous basis highly fragrant blossoms that are near white suffused with orange-pink in coloration, (c) forms attractive dark green decorative semi-glossy foliage that contrasts well with the blossom coloration, and (d) is particularly well suited for growing as attractive ornamentation in the landscape;

substantially as illustrated and described.

* * * * *

MEIGROLIP4